United States Patent [19]
Williams

[11] 4,197,755
[45] Apr. 15, 1980

[54] ROTARY DRIVE SYSTEMS

[75] Inventor: Anthony M. Williams, Iver, England

[73] Assignee: EMI Limited, Hayes, England

[21] Appl. No.: 856,603

[22] Filed: Dec. 1, 1977

[30] Foreign Application Priority Data

Dec. 23, 1976 [GB] United Kingdom .............. 53923/76

[51] Int. Cl.² ............................................ F16H 27/04
[52] U.S. Cl. ...................................... 74/84 R; 74/427
[58] Field of Search ....................... 74/84 R, 426, 427

[56] References Cited

U.S. PATENT DOCUMENTS

| | | | |
|---|---|---|---|
| 1,037,205 | 9/1912 | Clark | 74/427 |
| 1,113,172 | 10/1914 | Fassett | 74/427 |
| 1,322,599 | 11/1919 | Montgomery | 74/427 |
| 1,603,557 | 10/1926 | Schleier | 74/427 |
| 3,049,017 | 8/1962 | McDonald et al. | 74/84 R |
| 3,778,614 | 12/1973 | Hounsfield | 250/362 |
| 3,848,477 | 11/1974 | Giandinoto | 74/425 |
| 3,946,234 | 3/1976 | Hounsfield | 250/363 |

FOREIGN PATENT DOCUMENTS 1938559 2/1970 Fed. Rep. of Germany .

Primary Examiner—Allan D. Herrmann
Attorney, Agent, or Firm—Cooper, Dunham, Clark, Griffin & Moran

[57] ABSTRACT

In radiographic apparatus of the kind known as computerized tomographic (CT) apparatus, a source of radiation is moved around a patient to irradiate the patients body from a plurality of directions. In certain types of CT apparatus the motion includes a stepped rotation. During each rotational step reaction forces are transferred to the fixed part of the apparatus and for rapid movements the reaction forces can become excessive. To reduce the reaction forces a compensating means is provided to oppose the reaction forces. This may be a resilient member such as a spring and may react against a member, such as a cam, which is shaped to adjust the compensating force to a suitable value.

14 Claims, 9 Drawing Figures

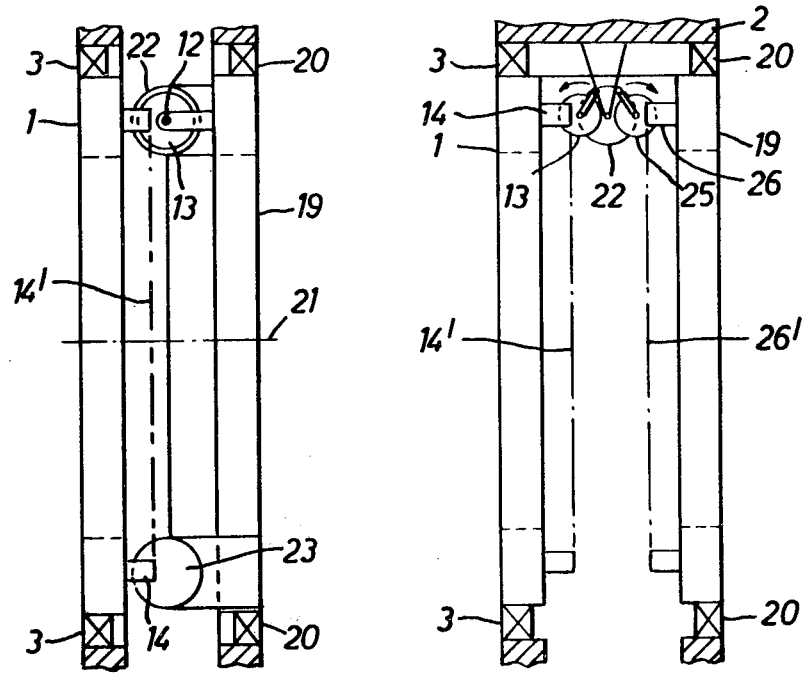
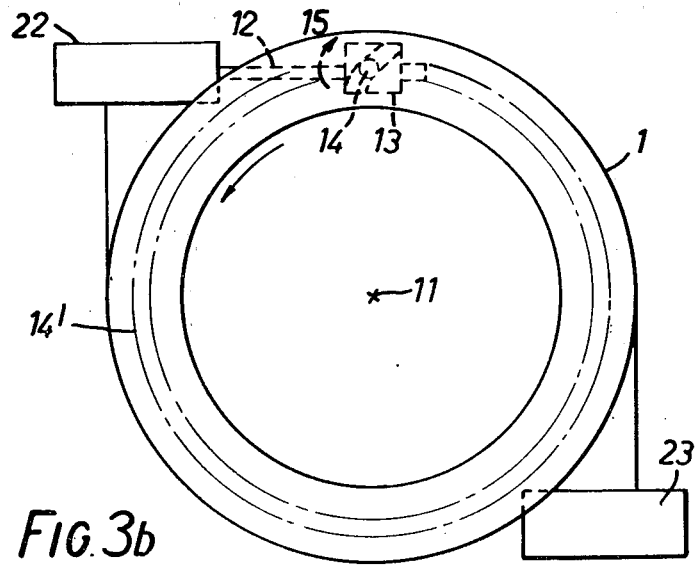

ROTARY DRIVE SYSTEMS

The present invention relates to rotary drive systems, and it relates especially, although not exclusively, to such systems as may be used for rotating a source of penetrating radiation, such as X-radiation, in steps around a body in the course of a computerised tomographic examination of the body.

Apparatus for performing computerised tomography is described, for example, in U.S. Pat. No. 3,778,614 and in one example of such apparatus a source of a single, pencil-like beam of the radiation is alternately scanned laterally across a slice of a body and moved angularly around the body through a small angle such as ½° or 1°. The motion of the source is followed by a detector, placed on the opposite side of the body to the source, so that the absorption suffered by the radiation on traversing each of many beam paths through the body can be determined. The absorption values so determined are processed to produce a representation of the absorption coefficient, with respect to said radiation, at each of many small locations distributed over the slice.

It is desirable in some circumstances for the absorption values to be acquired more rapidly than they can be when using the kind of apparatus utilising a single beam of radiation. It has been disclosed in U.S. Pat. No. 3,946,234 that it is possible to replace the aforementioned single beam of radiation with a fan-shaped spread of radiation subtending an angle of, for example, 10° and by distributing an array of, say, thirty detectors across the breadth of the spread so that when the source and detectors are scanned laterally across the slice each of the thirty detectors produces a respective series of signals relating to a respective set of parallel beam paths through the body. The angular movements can thus be made through steps of 10° (in this example) and thus the scanning procedure may be effected much more rapidly than in the case, previously described, in which a single beam is used, whilst maintaining dosage levels and signal-to-noise ratios of the absorption values substantially unchanged. A typical scan time for a computerised tomographic apparatus using a 10° spread of radiation as described in this paragraph is twenty seconds (EMI-Scanner computerised tomographic system Model CT5005).

Requirements exist for even faster scan times, however, and since the aforementioned scanning technique has proved to be reliable in practice it is desirable to utilise the same technique, suitably modified, to effect the faster scanning. Prima facie, it would appear straightforward to speed up the scanning described in the preceding paragraph by extending the fan angle of the spread of radiation and performing angular movements through the new, larger, angle. Indeed, in the example of the invention to be described hereinafter, the fan angle and the angular movements, are both extended to 20°. However difficulty can arise in some circumstances due to excessive torques which can be generated in moving the relatively massive source and detectors, on a scanning gantry, rapidly through an angle such as 20°.

According to the invention there is provided a rotary drive system, arranged to provide an intermittent rotation of a rotatable member about its axis of rotation in relation to a fixed frame of reference, the system including: an indexing mechanism arranged to apply an intermittent tangential force to the rotatable member and compensating means arranged to apply a force opposing the reaction, of the rotatable member on the indexing means, to reduce the force of reaction in relation to the fixed frame of reference.

In order that the invention may be clearly understood and readily carried into effect examples thereof will now be described with reference to the accompanying drawings of which:

FIGS. 1a and 1b show, in end and side elevation, a simplified form of the arrangement of U.S. Pat. No. 3,946,234, FIG. 2 shows an indexing mechanism suitable for use with the invention, FIGS. 3a and 3b show, in side and end elevation respectively one example of the invention, FIG. 4 shows an alternative to the arrangement of FIG. 2

The arrangement described herein may be comprise part of an X-ray apparatus such as that described and claimed in U.S. Pat. No. 3,946,234 which is incorporated herein by reference.

Figures 1A, 1B:
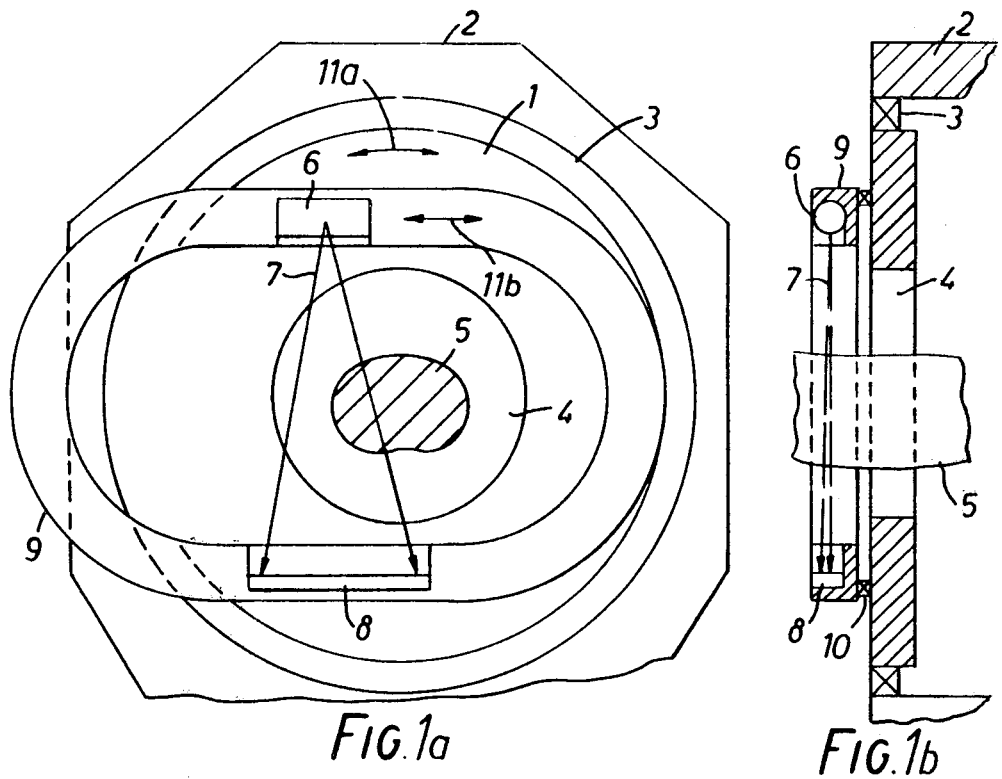

There is shown in FIGS. 1a and 1b, in front and side elevation respectively, a simplified form of the apparatus disclosed in U.S. Pat. No. 3,946,234. The apparatus comprises a rotary member 1 which is rotatable inside a fixed mainframe 2 of the apparatus, on suitable means, in this example a bearing 3. The rotary member 1 has a central aperture 4 in which the body 5, of a patient to be examined, is placed. The member 1 carries a source 6 of a substantially planar fan-shaped distribution 7 of radiation and an array of detectors 8 on which the radiation is incident. The detectors provide output signals indicative of the intensity of radiation incident on them. The source 6 is linked to the detectors 8 by a lightweight but rigid yoke 9, and source 6, detectors 8 and yoke 9 are capable of a linear motion, relative to member 1, on bearings 10.

Respective drive means, not shown, provide a rotary motion, indicated by arrow 11a, of member 1 and the elements mounted thereon relative to main frame 2 and a traverse motion, indicated by arrow 11b of yoke 9 and the elements fixed thereto relative to member 1. The drive means may be electric motors operating through gear wheels or drive belts as appropriate. Typically the rotation is stepped and a traverse motion is provided while the member 1 is stationary between each rotational step. In that case the rotation may be provided by a stepping motor or by a continuously driven motor via a stepping mechanism such as, for example, the well-known "geneva" mechanism, or the arrangement to be described with reference to FIG. 2.

It is the stepped arrangement to which the present invention relates so that excessive reaction on mainframe 2 can be avoided for larger rotational steps of the member 1.

Figure 2:
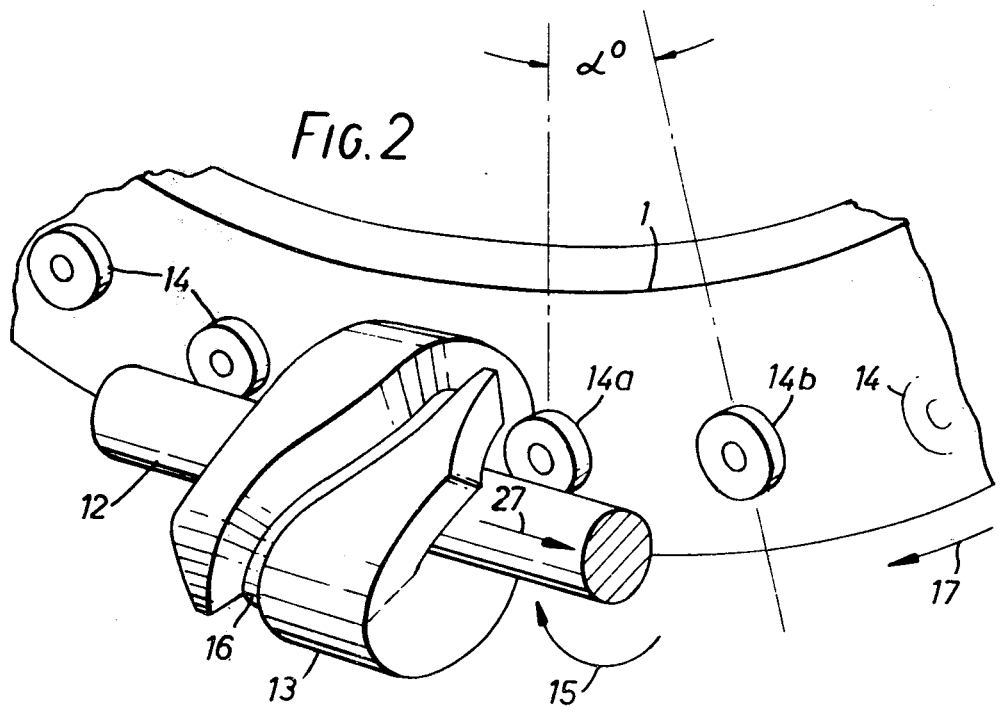

FIG. 2 shows a suitable indexing rotary drive for imposing an intermittent rotary motion, through an angle α, on a ring shaped rotary member 1 of which only part is shown. A drive shaft 12, rotated at a substantially constant speed by a motor not shown, carries a cam member 13. The ring member 1 carries on one side cam followers 14 accurately placed so that their centres lie on diameters of member 1 which are angularly displaced from each other by the angle α, in this example 20°.

In operation the motor drives shaft 12 and cam member 13 in one direction, in this example indicated by arrow 15. Cam follower 14a will then enter a helical drive track 16 of the cam and be driven, in the direction shown in FIG. 2 by arrow 17, through angle α. When follower 14a is released from the track 16 the next follower 14b will be in a suitable position to be captured on the next revolution of cam member 13.

This form of intermittent drive mechanism is well known in various forms. It will be understood that it can be replaced by other mechanisms, for converting a steady rotation of shaft 12 into an intermittent rotation of member 1, such as the Geneva mechanism previously mentioned. Shaft 12 can be in a different disposition in relation to member 1 as required.

As mentioned hereinbefore, however, the reaction forces generated through shaft 12 in moving member 1 can be large and it is undesirable to allow such forces between moving parts of the apparatus and its fixed main frame.

In one example of the present invention it is proposed to mount the motor driving shaft 12 on a second rotary member coaxial with member 1. FIGS. 3a and 3b show the resultant arrangement in side and end elevation respectively, the mainframe 2 not being shown in the front elevation of FIG. 3b.

Ring member 1 is shown supported by the bearings 3 and a second ring member 19 is placed alongside supported by bearings 20 so as to be capable of rotation about the same axis 21. Ring member 19 carries the motor 22 driving shaft 12 and diametrically opposite a counterweight 23 so that motor 22 and cam 13, together with necessary mounts and bearings, do not impose out of balance rotational forces on member 19.

In this example cam member 13 and cam followers 14 are arranged to provide a rotational step of 2 α. Only one follower 14 is shown the remainder being indicated by the bounds 14'. Members 1 and 19 are free moving on their respective bearings and should have equal moments of inertia for rotation, including the X-ray equipment, motors and other equipment mounted thereon. In that case the stepped motion will divide itself equally between the two ring members. The member 1 carrying the X-ray source etc. will move through the desired angle α in one direction and ring member 19 through angle α in the other direction.

Clearly this evenly divided motion is critically sensitive to changes in the inertia of the system and provision should be made for trimming masses.

The sensitivity to inertia can be avoided by an alternative arrangement, shown in FIG. 4, at the expense of a slight transfer of forces to the static main frame. In this alternative the motor 22 is fixed to the main frame 2 and drives a second cam member 25. Cam member 25 drives cam followers 26 on rotary member 19, facing member 1 and cam members 13 and 25 are driven via a gear box so as to rotate in opposite directions. Thus rotary members 1 and 19 are simultaneously stepped through the angle α in opposite directions and although out of balance forces are transmitted to the main frame 2 these are much reduced compared with the known arrangement.

A further alternative and preferred arrangement mounts motor 22 and cam member 13 on the main frame 2, stepping through angle α as in FIGS. 2 and 4, but dispenses with rotary member 19. The arrangement is thus essentially that of U.S. Pat. No. 3,946,234 using the stepping drive of FIG. 2 and consequently reaction forces can be transmitted to the mainframe 2 via motor 12. A shock absorber is therefore provided in this example of the invention to absorb the forces which would otherwise be transmitted via motor 12.

It can be seen from FIG. 2 that the action, of cams 14 on cam follower 13, imposes on shaft 12 a force in the direction of arrow 27. This is a large force in view of the inertia of member 1. It is therefore proposed to mount on shaft 12 a second cam capable of applying an opposing force at the same stage of the shaft's rotation.

Figure 5:
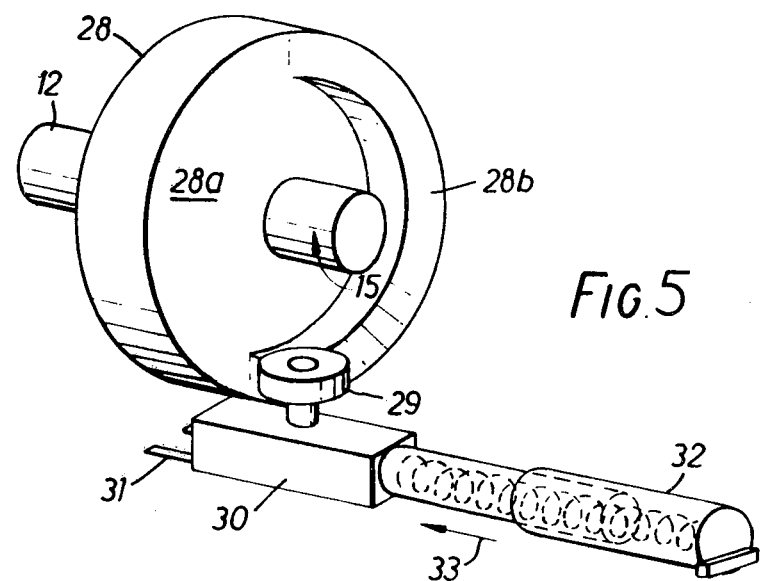
FIG. 5 shows another example of the invention.

FIG. 5 shows a detail of the opposing cam 28. A cooperating cam follower 29 is mounted on a sliding member 30 sliding, in tracks 31 in main frame 2, parallel to the axis of shaft 12. A telescopic member 32, which may include a spring or hydraulic means or similar, is positioned so as to exert a force on member 30, and via cam follower 29 on cam 28, in the direction of arrow 33.

The arrangement is such that cam follower 29 exerts substantially no force on cam 28 when in contact with the recessed surface 28a. However, when cam 28 is pushed back by raised surface 28b, the member 32 causes it to exert a force substantially the same as the force exerted by followers 14 on cam 13. These two forces are, however, arranged to be opposite and substantially cancelling, cams 28 and 13 being phased so that the forces are properly opposed. Of course the force exerted on cam 28 need not exactly compensate the reaction force but it is beneficial if it can at least reduce that force.

Figure 6A:
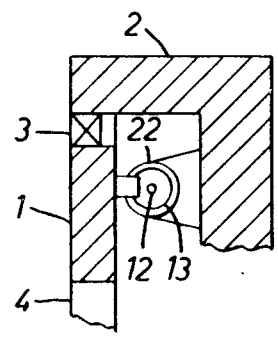
FIGS. 6a and 6b show details of the mounting of the FIG. 5 arrangement.
Figure 6B:
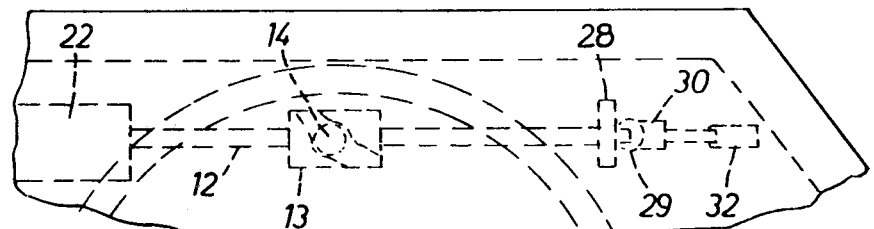

To accommodate the mechanism of FIG. 5, the main frame 2 should be extended behind member 1, compared with the arrangement of FIGS. 1, 3 and 4. FIGS. 6a and 6b show details of the side and end elevations of the apparatus, indicating a suitable extension of frame 2.

Clearly the cam 28 need not be mounted on the same shaft 12 as cam 13 provided it is placed so as to be capable of substantially cancelling the forces applied to the main frame 2.

Other possible arrangements will be apparent to those skilled in the art.

What I claim is:

1. A rotary drive system, arranged to provide an intermittent rotation of a rotatable member about its axis of rotation in relation to a fixed frame of reference, the system including: indexing means for applying an intermittent tangential force to the rotatable member, and compensating means for applying to the indexing means a force opposing the reaction, of the rotatable member on the indexing means, to reduce the force of reaction in relation to the fixed frame of reference.

2. A rotary drive system according to claim 1 including a motor having a continuously rotating shaft for driving the indexing means.

3. A rotary drive system according to claim 1 in which the compensating means includes a resilient member and means for utilizing the resiliency thereof for reducing said force of reaction.

4. A rotary drive system, arranged to provide an intermittent rotation of a rotatable member about its axis of rotation in relation to a fixed frame of reference, the system including: an indexing means for applying an intermittent tangential force to the rotatable member, and compensating means including a cam member, moving in synchronism with the indexing means, and a resilient member arranged to exert on the cam member, at different stages of its motion, a force opposing the reaction, of the rotatable member on the indexing means, to reduce the force of reaction in relation to the fixed frame of reference.

5. A rotary drive system according to claim 4 including means for mounting the cam member in a fixed relation to the indexing means.

6. A rotary drive system according to claim 5 including a motor having a rotatable shaft for driving the indexing means and wherein the cam member rotates on the shaft of said motor.

7. A rotary drive system according to claim 4 in which the resilient member is a spring mechanism.

8. A rotary drive system according to claim 4 in which the compensating means includes means for applying a force substantially equal and opposite to the said reaction on the indexing means to substantially prevent a force of reaction in relation to the fixed frame of reference.

9. A rotary drive system according to claim 4 including a motor having a continuously rotating shaft for driving the indexing means.

10. A rotary drive system, arranged to provide an intermittent rotation of a rotatable member about its axis of rotation in relation to a fixed frame of reference, the system including: an indexing means for applying an intermittent tangential force to the rotatable member, and compensating means comprising a second rotatable member, rotatably mounted on the same axis as the first rotatable member, in which the indexing means includes means for causing said rotatable members to receive opposing intermittent tangential forces causing them to rotate in opposite directions in relation to the fixed frame of reference in order to reduce the force of reaction caused by the indexing means in relation to the fixed frame of reference.

11. A rotary drive system according to claim 10 including a motor having a continuously rotating shaft for driving the indexing means.

12. A rotary drive system according to claim 10 in which the indexing means is fixed relative to said frame of reference.

13. A rotary drive system according to claim 9 in which the rotatable members have substantially equal moments of inertia, taking into account equipment mounted thereon so that the opposing tangential forces cause the rotatable member to rotate through substantially equal and opposite angles.

14. A rotary drive system according to claim 13 in which the indexing means is mounted on the second rotatable member and indexes the first rotatable member, relative to the second rotatable member, through twice the angular step of the first rotatable member relative to the frame of reference.

* * * * *